(12) United States Patent
Choncholas et al.

(10) Patent No.: US 8,881,724 B2
(45) Date of Patent: Nov. 11, 2014

(54) DEVICE AND METHOD FOR GRAPHICAL MECHANICAL VENTILATOR SETUP AND CONTROL

(75) Inventors: Gary J. Choncholas, Madison, WI (US); Paul R. Micheli, Monona, WI (US); Jaron M. Acker, Madison, WI (US); Robert Q. Tham, Middleton, WI (US)

(73) Assignee: The General Electric Company, Schenectady, NY (US)

( * ) Notice: Subject to any disclaimer, the term of this patent is extended or adjusted under 35 U.S.C. 154(b) by 2255 days.

(21) Appl. No.: 11/550,989

(22) Filed: Oct. 19, 2006

(65) Prior Publication Data
US 2008/0185009 A1    Aug. 7, 2008

(51) Int. Cl.
*F16K 31/02* (2006.01)
*A61M 16/00* (2006.01)
*A61B 17/00* (2006.01)

(52) U.S. Cl.
CPC ...... *A61M 16/00* (2013.01); *A61B 2017/00199* (2013.01); *A61M 2205/502* (2013.01)
USPC ............. 128/204.21; 128/200.24; 128/204.18

(58) Field of Classification Search
CPC ............ A61M 16/00; A61M 16/0051; A61M 2016/0021; A61M 2016/0039; G06F 3/0481–3/0483
USPC .......... 128/204.21, 897, 898, 204.18, 200.24, 128/204.23, 202.22, 204.22, 205.23; 600/529, 533, 538; 715/736, 747, 771
See application file for complete search history.

(56) References Cited

U.S. PATENT DOCUMENTS

| | | | | | |
|---|---|---|---|---|---|
| 5,752,509 | A  * | 5/1998 | Lachmann et al. | ...... | 128/204.23 |
| 6,463,930 | B2 * | 10/2002 | Biondi et al. | ............ | 128/204.21 |
| 2001/0035186 | A1* | 11/2001 | Hill | ........................ | 128/204.18 |
| 2003/0045807 | A1* | 3/2003 | Daniels et al. | ................ | 600/538 |
| 2003/0230308 | A1* | 12/2003 | Linden | ..................... | 128/204.18 |
| 2004/0118404 | A1* | 6/2004 | Wallace et al. | ........... | 128/205.23 |
| 2007/0163584 | A1* | 7/2007 | Bohm et al. | ............. | 128/204.18 |
| 2009/0055735 | A1* | 2/2009 | Zaleski et al. | ................ | 715/700 |

OTHER PUBLICATIONS

General Electric Company, Datex-Ohmeda Anethesia Delivery Unit: User's Reference Manual. May 6, 2003.

* cited by examiner

*Primary Examiner* — Justine Yu
*Assistant Examiner* — Colin W Stuart
(74) *Attorney, Agent, or Firm* — Andrus Intellectual Property Law, LLP

(57) ABSTRACT

An input device for a clinician to control and modify the operation of a mechanical ventilator comprises a graphical display, a representation of a respiratory therapy trajectory to be delivered to a patient, at least one data point associated with the trajectory, and a data input means for the clinician to select a data point and to modify the value of the trajectory at that data point. The present invention provides for the creation and modification of a respiratory therapy trajectory, wherein the ventilator provides a medical gas waveform to a patient according to the respiratory therapy trajectory.

18 Claims, 12 Drawing Sheets

DEVICE AND METHOD FOR GRAPHICAL MECHANICAL VENTILATOR SETUP AND CONTROL

FIELD OF THE INVENTION

The present invention relates to the field of mechanically assisted patient ventilation. More specifically, the present invention relates to a new method and device for a clinician to use in modifying specific aspects of the respiratory therapy that is to be provided by the mechanical ventilator to the patient. By the present invention, a clinician is able to intuitively interact with the mechanical ventilator to create a new respiratory therapy, thereby increasing the efficiency of the selection and implementation of the desired respiratory therapy.

BACKGROUND OF THE INVENTION

Mechanical ventilation is a commonly accepted medical practice for the treatment of individuals experiencing respiratory problems. These patients may not be spontaneously breathing at all, such as a patient that may be in an intensive care unit. In these instances, mechanical ventilation is provided according to a clinician defined respiratory therapy trajectory. Alternatively, the patient may be too weak from disease and/or sedated from an anesthetic agent to complete an entire respiratory cycle under his own power. In these instances, mechanical ventilatory assistance is provided whereby patient spontaneous breath attempts are detected by the ventilator using transducers placed in the ventilator breathing circuit to detect when the patient spontaneously attempts to breathe.

A respiratory therapy trajectory describes a ventilator delivery to achieve a desired ventilatory result and can be defined by a time varying-pathway or a combination of the necessary vent settings. For example, the time-varying pathway can be the inspiratory flow or airway pressure patterns of the ventilator. Examples of the vent settings include but are not limited to: tidal volume, respiration rate, inspired and expired duration, inspiratory and positive end-expiratory pressures that are common to ventilator settings, pressure overshoots, and rise times. The respiratory therapy trajectory determines the delivery of the ventilation therapy. The respiratory therapy trajectory is to be distinguished from the measured respiratory therapy waveform, as the respiratory therapy waveform is the measured effect of the ventilation therapy set according to the selected delivery trajectory. In general operation a clinician will create a trajectory, the respiratory therapy will be delivered according to the trajectory and a sensor will measure the resulting waveform.

A patient receiving mechanical ventilation may also receive therapeutic treatment from the way in which the mechanical ventilator delivers the respiratory therapy. Modification of various parameters of the mechanical ventilator can help to improve patient respiratory function. These modifications may include modifications to the respiratory therapy trajectory of medical gas that is delivered to the patient for each patient breath, modifications to the various patterns of changing ventilatory pressures, the addition of supplemental medical gases to the requisite air for the ventilation, and the length and/or combination of any of these and other treatment modifications. Specifically, modifying the pressure at which medical gas is delivered until the ventilator cycles to an expiratory phase can help improve patient lung function. In this form of treatment, different patterns of changing ventilatory pressure can produce different results and as such the clinician must tailor a respiratory therapy trajectory to a patient to ensure that the patient receives the proper treatment.

There are several limitations, however, associated with current ventilatory systems and the means by which the respiratory therapy trajectories may be modified for the clinician to provide the proper respiratory therapy to the patient. Under currently available ventilatory systems, the clinician must enter the respiratory therapy trajectory data by entering ventilatory parameters in numerical form into the ventilator controls. Additionally, a clinician scrolls through a table to choose the parameter of interest. Upon selecting the parameter the trajectory is displayed. The user can change this parameter through the menu updating the trajectory. Finally, the user confirms the desired setting which also navigates them back to the table of parameters. This approach only allows one parameter to be modified through this sequence of menu operations. This tedious sequence of steps must be repeated to change additional parameters. These processes are difficult for the clinician because it requires pre-computation of many of the ventilatory parameters as well as the management of these ventilatory parameters. Furthermore, the clinician must visualize the trajectory or sketch it on a piece of paper since there is no visual feedback as to the trajectory that the clinician is creating. Additionally, current ventilatory systems do not provide the clinician with feedback comprising the resulting effects that the modification of the ventilatory parameters by the clinician has on other parameters of the ventilatory system. Therefore, the clinician does not know, unless further calculations are performed, the full extent of the effect a parameter selection may have on ventilator function. The creation of a trajectory with tabular data places a greater cognitive load on the clinician as opposed to creating the trajectory graphically.

Furthermore, ventilator systems produced by different companies use different names for respiratory therapy trajectories. This may confuse a clinician who must switch between various ventilator platforms. Alternatively, respiratory therapy trajectories with similar names may function differently across ventilator platforms. These differences make it difficult for clinicians to operate and/or become proficient at the use of multiple brands of ventilators.

Therefore, it is desirable in the field of mechanical ventilator systems for an intuitive interface where a clinician can easily graphically modify a ventilation parameter. Furthermore, it is desirable that upon the entry of a modification to a ventilatory parameter, the clinician be presented with the ventilatory operation consequences of the modification to the parameter. It is also desirable for an improved method for the entry of desired modifications to the therapeutic ventilatory pressure trajectory, such that it is easy to modify the pressure trajectory to individually tailor a ventilatory pressure treatment to the patient. Finally, it is desirable to provide a mechanical ventilator user interface that allows the clinician to define the name of the newly created and saved respiratory therapy trajectory.

SUMMARY OF THE INVENTION

By the present invention, a user interface is provided for the control of a mechanical ventilator that promotes the design of custom respiratory therapy trajectories such as vent setup trajectories and vent procedure trajectories. The vent setup trajectory shapes the breath delivered by the ventilator. The vent procedure defines the sequence of multiple breaths or other events delivered by the ventilator. The user interface of the present invention allows the clinician to create the respiratory therapy trajectory and visually observe the trajectory in graphical form as the clinician creates the trajectory. Alternatively, the clinician can select from a variety of standard or model vent setup or vent procedure trajectories, and modify these trajectories to specifically tailor the respiratory therapy to the needs of the patient. As the clinician modifies a parameter of the trajectory to be delivered to the patient, the interface of the present invention displays back to the clinician a numerical setting that is dependent upon the modifications made by the clinician such that the clinician is made aware of the effects of the modification of a particular ventilator setting.

In an embodiment of the present invention, the clinician creates the vent setup trajectory by dragging and dropping data points to create the desired trajectory. In a further embodiment, the clinician modifies the vent setup trajectory by selecting data points and modifying the values at these points.

In an embodiment of the present invention, the clinician creates the vent procedure trajectory by dragging and dropping data points to create the desired trajectory. In a further embodiment, the clinician modifies the vent procedure by selecting the data points and modifying the values at these points.

In an embodiment of the present invention, the clinician names and saves the respiratory therapy trajectory created by the clinician, such that the saved respiratory therapy trajectory may be used again at a later date without having to recreate the trajectory.

In a further embodiment of the present invention, the input device displays at least one numerical value and modifies that numerical value in relation to any changes made to the data points of the respiratory therapy trajectory by the clinician.

In still a further embodiment of the present invention, the data points of the vent procedure are indicative of ventilation pressures and number of breaths.

In still a further embodiment of the present invention, the data points of the vent procedure are indicative of ventilation volume and number of breaths.

Another embodiment of the present invention comprises the user input device of the present invention skins the underlying ventilator controller, such that the input device works with a plurality of ventilator units. A skin is a popular term for changing the appearance of an application without altering the underlying functionality.

In another embodiment of the present invention, the graphical user interface of the present invention displays a synchronous display of recorded patient physiological parameters and respiratory therapy trajectory progress.

A method is herein disclosed whereby a clinician modifies a respiratory therapy trajectory parameter and observes the ventilatory effects of the modification of the parameter and further modifies a parameter in response to the displayed ventilatory effects.

The method of the present invention further includes the step of selecting data points associated with the respiratory therapy trajectory to be delivered to the patient and modifying the values of the data points to create the respiratory therapy trajectory based off of the selected data points.

DETAILED DESCRIPTION

Figure 1:
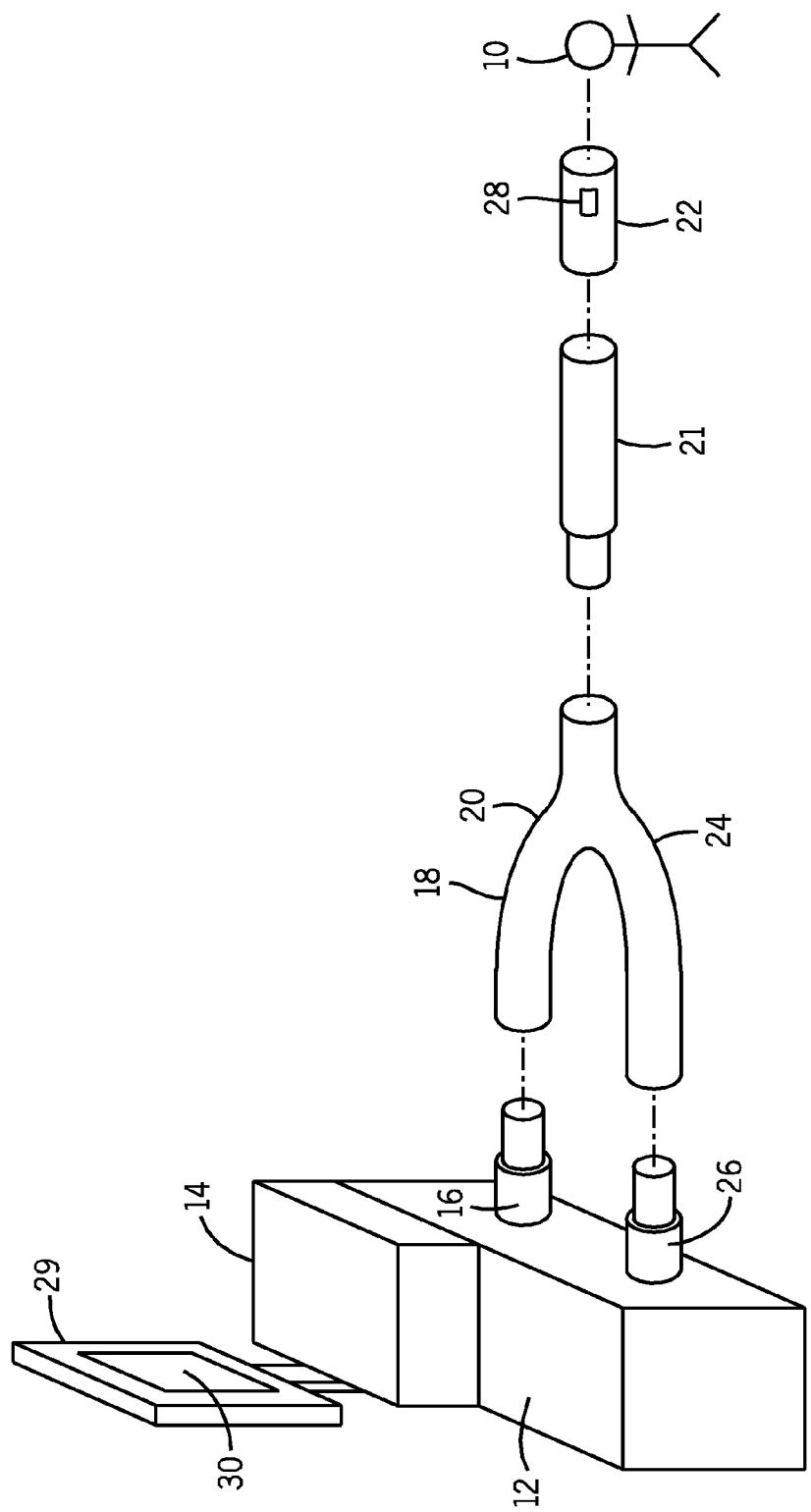
FIG. 1 depicts an embodiment of the present invention connected to a ventilator system.

FIG. 1 depicts a ventilatory system comprising the user input device 29 of the present invention. A patient 10 receives respiratory therapy from a mechanical ventilator 12 through a series of connected pneumatic tubes. Typically, the ventilator 12 comprises a controller 14 that operates the ventilator 12 to deliver the proper respiratory therapy to the patient 10. This respiratory therapy is delivered to the patient according to a respiratory therapy trajectory. A clinician then monitors the waveform of medical gas produced within the ventilator system by the controller 14 following the trajectory. Typically, the controller 14 will be a CPU; however, it is understood that other forms of microcontrollers and/or microprocessors may be used in accordance with this invention.

In delivering a breath of medical gas to the patient 10, the ventilator 12 sends a flow of medical gas through an inspiratory port 16 where it enters the inspiratory limb 18 of a breathing circuit 20. The breathing circuit 20 directs the medical gas into a patient limb 21 where it is further directed through a patient connection 22 that is disposed to engage the patient 10 such that the medical gas is delivered to the patient's lungs. Typical patient connections that may be used in accordance with this invention would be a face mask, an endotracheal tube, a nasal cannula, or a pneumatic helmet; however, other suitable patient connections exist and can be used in accordance to the present invention. A pressure transducer 28 is disposed proximal to the patient connection 22 to monitor the pressure at the patient connection. The pressure transducer 28 may be integral with the patient connection 22 or may be a separate component. The medical gas enters the lungs and inflates the lungs, thus exposing the alveoli of the lung to the medical gas.

When the supply of medical gas from the ventilator 12 ends, the natural compliance of the patient's lungs and chest wall will collapse, allowing the patient to passively exhale in an expiratory phase. The exhaled gas is directed back through the patient connection 22, patient limb 21, and the breathing circuit 20; however, check valves (not depicted) disposed within the breathing circuit 20 direct the exhaled gas through the expiratory limb 24 of the breathing circuit 20. The exhaled gas is returned to the ventilator 12 through an expiratory port 26. Once in the ventilator 12, the exhaled gas is exhausted to the ambient air via an exhalation valve (not depicted). It is also understood that other configurations of the pneumatic connections with the patient 10 may be used in accordance with the present invention. For example, an embodiment that vents or exhausts the exhaled gas to the air directly from the patient 10 or the patient connection 22.

The term "medical gas" as used in this application refers to any gas or combinations of gases that are delivered to a patient in a clinical setting. Most commonly, the medical gas delivered to the patient is air. In other instances, the air is combined with a supplemental gas or gases which provide increased physiological or therapeutic support with the mechanical ventilation. These included gases may be gases such as oxygen, helium, nitrous oxide, an anesthetic agent, or a drug aerosol. However, this list is merely exemplary of the types of supplemental gases that may be used in accordance with the present invention and is not intended to be limiting to the scope of the present invention.

The clinician uses input device 29 to enter the parameters and values into the ventilator controller 14 to create a respiratory therapy trajectory for providing the proper ventilatory waveform to the patient 10. The input device 29 comprises a display 30 for displaying patient information and ventilator information to the clinician. The clinician can also view the respiratory therapy to be provided to the patient in accordance with the present invention. The input device 29 further comprises an input means (not depicted) whereby the clinician can modify patient data or the respiratory support to be provided to the patient. The input means may include, but is not limited to, buttons, soft keys, a mouse, dials or knobs, a keyboard, or touch screen technology; but other suitable input means may be used in accordance with the present invention.

Often, ventilators created by different manufacturers have fundamentally different input devices 29, such that the ventilator settings and modes vary between ventilator brands. Ventilator controllers 14 from different companies may refer to the same parameter by different names or parameters with similar names may be very different in operation. Therefore, an embodiment of the input device 29 of the present invention is designed as a skin that operates over the ventilator controller 14. This enables the input device 29 to operate using the graphical representation of data and controls to consistently operate many different ventilator machines. This promotes efficiency with clinicians only needing to know one system to operate many different mechanical ventilators.

Figure 2:
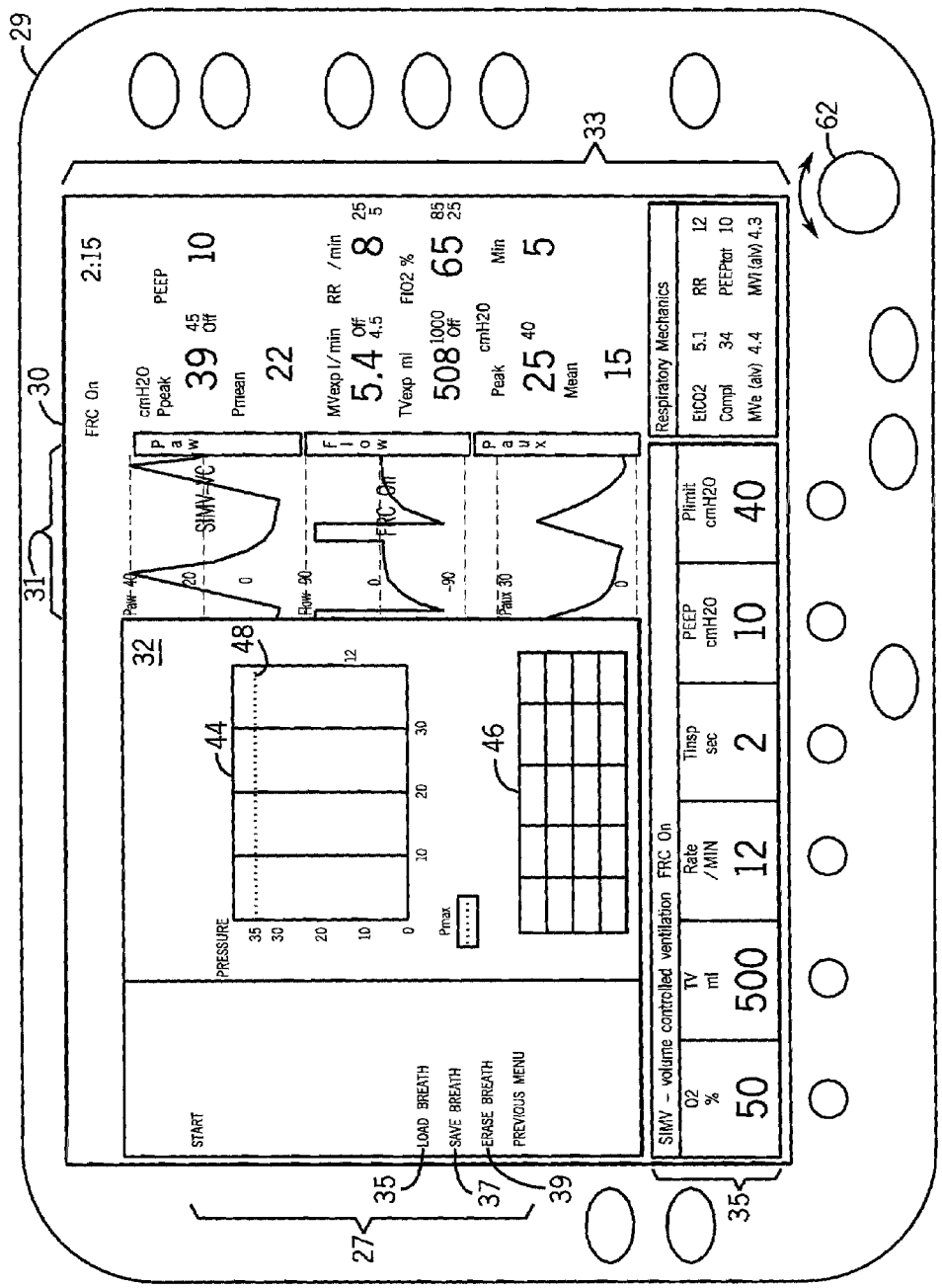
FIG. 2 depicts an embodiment of the user interface of the present invention.

FIG. 2 is a depiction of the input device 29 of the present invention. The input device 29 comprises a display 30 that displays the ventilator information to a clinician. This information comprises a variety of graphical 31 and numerical 33 representations of current ventilation parameters monitored by the ventilator. The GUI 32 is displaying the controls for establishing a respiratory therapy trajectory. The respiratory therapy trajectory may be modified by selecting one of the procedure variable buttons 27 of the GUI 32. The selection of one of the buttons 27 allows the clinician to perform an operation within the GUI 32. These operations may include loading a trajectory 35, saving a newly created trajectory 37, or erasing a trajectory 39. Other controls (not depicted) may be selected to enter numerical values for ventilation settings. The numeric values of these ventilation settings may be displayed in a table 46 at the bottom of GUI 32 with corresponding headings.

In an embodiment of the present invention, the ventilation parameter values are displayed in tabular form in table 46, and are displayed in a graphical form on graph 44. Graph 44 may display information from table 46, but in a graphical fashion. A ventilation parameter indicator for Pmax 48, corresponds to a graphical representation on the graph 44. The display of the respiratory therapy trajectory to the clinician in an intuitive fashion allows the clinician an overall view of the respiratory therapy trajectory depicting the changes to the ventilation settings during the creation of the trajectory.

The present invention will be herein further described in greater detail by the exemplary explanation of the present invention with respect to two different embodiments of the present invention. The first embodiment describes the operation of the present invention for creating and/or modifying a vent setup trajectory of a mechanical ventilator. The second embodiment describes the operation of the present invention for creating and/or modifying a vent procedure trajectory that concatenates a string of vent setup trajectories to construct and control a sequence of ventilation breaths or events to achieve an intended respiratory treatment or outcome. However, it is understood that the present invention may be used to create and/or modify any other respiratory therapy trajectories associated with the provision of mechanical ventilation to a patient.

Vent Setup

Typically, there are two broad categories of mechanical ventilation modes. The first mode is fixed-volume ventilation. In fixed-volume ventilation, the patient is prescribed a particular volume of medical gas to be delivered, typically but not always, during a prescribed inspiratory time in each respiration cycle. A flow meter placed in the patient connection monitors the flow of medical gas and the gas flow rate is integrated to monitor the total volume delivered to the patient. In an embodiment, a flow valve (not depicted), located in ventilator 12, is controlled to deliver medical gas that tracks a prescribed flow trajectory. The flow trajectory can be as simple as a constant flow rate delivered over the inspiratory time. The amplitude of the flow trajectory may be fixed, or computed from the relationship of the desired tidal volume and inspiration time, such as a ratio. Alternatively, the flow amplitude can be referenced to a measured target such as the tidal volume integrated from the flow meter and during delivery, the flow rate can be adjusted breath-to-breath to achieve the prescribed volume of medical gas to be delivered at the prescribed inspiratory time. When the prescribed inspiratory duration is delivered, the ventilator cycles to an expiratory phase. In this instance, the invention pertains to the design and delivery of the medical gas flow out of the ventilator flow valve within a breath cycle, in accordance to a vent setup trajectory that directly commands the ventilator flow valve.

The second ventilation mode is a pressure-controlled ventilation mode. In pressure-controlled ventilation, the patient is prescribed a particular inspiratory pressure of medical gas to be delivered in each respiration cycle. The flow rate is initially high to achieve the inspiratory pressure. Once that pressure is achieved, the flow decelerates to cover leaks. In pressure-controlled ventilation, the pressure transducer 28 disposed in the patient connection 22 monitors the pressure of the medical gas experienced by the patient. The mechanical ventilator 12 via controller 14 controls the flow of medical gas out of the ventilator flow valve such that the inspiratory pressure measured by pressure transducer 28 tracks the prescribed pressure trajectory over the course of the breath. In an embodiment the user interface 29 is used to design the pressure trajectory that the controller 14 uses as the feedback input to command the ventilator flow valve to deliver the appropriate medical gas flow for the measurement of the pressure transducer 28 to track the prescribed vent setup trajectory. Vent setup trajectories, prescribed over a breath, may be associated with any referenced signal from a ventilator related transducer. Examples of such transducers may include, but are not limited to, pressure sensors at the airway or endotracheal tube, and flow sensors at the inspiratory limb or endotracheal tube.

Respiratory therapy may be delivered according to the vent setup trajectory and the controller may measure and monitor the resulting waveform that is delivered to the patient. Some controllable inputs are: pressure, flow, and volume, any of which may be made the trajectory and the resulting effect to the others may be observed as a waveform.

Figure 3A:
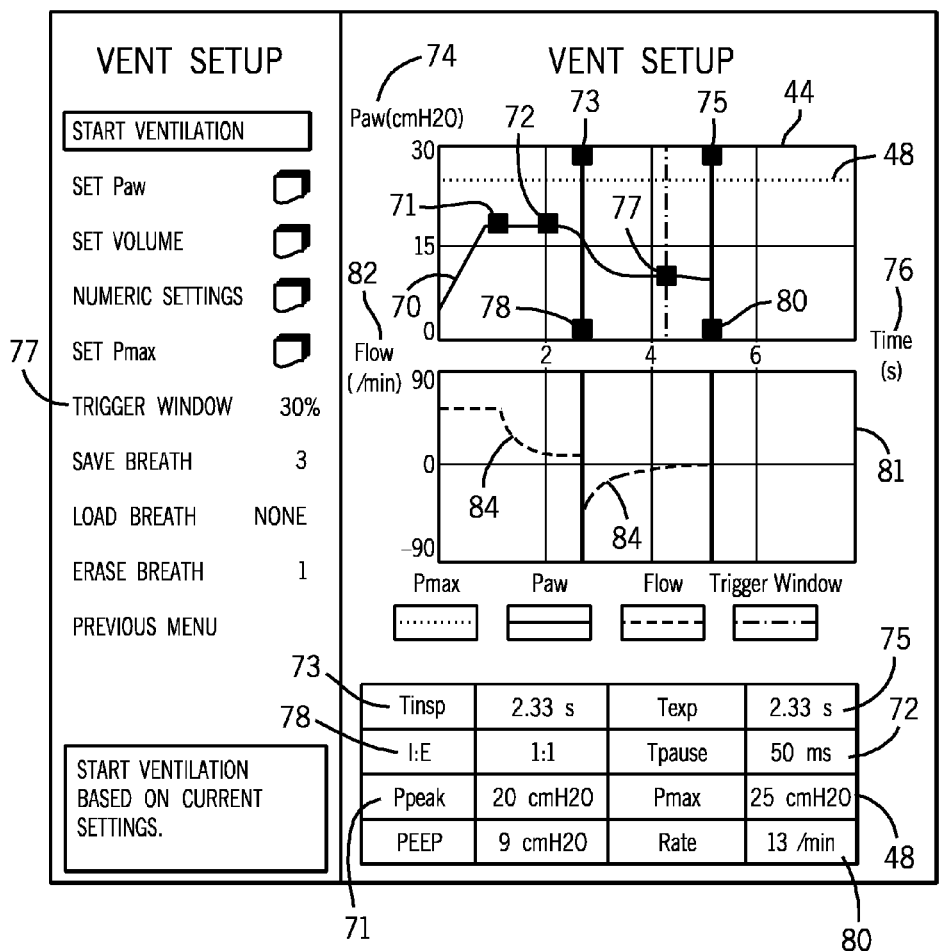
FIG. 3A depicts a screen shot of an embodiment of an interface for a clinician to create or modify a respiratory therapy pressure trajectory.

FIG. 3A depicts a screen shot of an embodiment of the GUI 32 that a clinician may use to create or modify a vent setup pressure trajectory. A graph 44 depicts an airway pressure (Paw) vent setup trajectory 70 that is created by the clinician. The graph depicts the level of Paw 74 of the vent setup trajectory 70 over time 76. The clinician creates the Paw trajectory 70 by dragging and dropping a plurality of data points, depicted in FIG. 3A as squares. In the embodiment of the present invention depicted, the data points are indicative of different vent setup parameters such as target airway pressure 71, pause initiation 72, inspiratory time (Tinsp) 73, expiratory time (Texp) 75, I:E ratio 78, SMIV triggering window 77, and respiration rate 80. It is understood that within the present invention, the data points may be placed or established in a variety of data entry methods such as point and click, arrow key movement, or cut and paste; however, these named embodiments are merely exemplary and not meant to be limiting as to the present invention. The data points are placed at the desired pressure level 74 and time interval 76 for that data point to occur in the vent setup trajectory 70. Corresponding numerical values for the data points appear in the table 46, representative of the settings of the ventilator.

In an embodiment of the present invention, the data points are placed at the vertices of the vent setup trajectory 70 and the trajectory 70 is created by connecting the data points linearly or nonlinearly taking into consideration the ventilator and patient dynamics. Alternatively, the data points may represent other parameters of the trajectory such as an exponent and amplitude values of a first order exponential trajectory.

After the data points have been placed on the graph 44, the values of the data points may be modified to change the pressure 74, or the time interval 76 associated with the data point. As a clinician modifies the values of the data points, values for the corresponding ventilation settings displayed in the table 46 may be modified to reflect the clinician's changes to the values of the data points. As the clinician modifies a value for a data point, the ventilation settings in the table 46 may change, indicating to the clinician the effects of the modified values of the data point. For example, if the clinician moves the expiratory time data point 75, the displayed respiration rate 80 will change to reflect breaths of the new time duration. Additionally, the I:E ratio will also change.

Alternatively, data points on graph 44 that are related will update in real time with the modification of one data point. For example, a clinician may modify the value of the time of inspiration 73. Because the time of inspiration 73 is related to time of expiration 75 by the I:E ratio 78, as the clinician modifies the value of the time of inspiration 73, the time of expiration 75, as well as the respiration rate 80 will change to maintain the set I:E ratio 78. Similarly, if a clinician modifies the I:E ratio 78, the time of inspiration 73 will also change accordingly, but the time of expiration 75 will not change as the desired I:E ratio 78 is obtained by solely modifying the time of inspiration 73.

Additionally, as the Paw trajectory 70 is created by the clinician, an estimate of the flow waveform 84 that will be delivered by be additionally created and displayed on a flow graph 81. Alternatively, the flow waveform 84 may be depicted on the graph 44. The flow waveform 84 depicts the flow level 82 with respect to time 76 over the course of the Paw trajectory 70. The estimate of the flow waveform may be created using the response of the patient and ventilatory system measured by the ventilator. Alternatively, the flow trajectory 84 may be created by inputting the Paw trajectory 70 into a transfer function representative of the patient-ventilator system. The estimated flow waveform 84 will also display to the clinician the effect of a modification of one or more data points of the pressure trajectory 70, on the estimated flow waveform 84, thereby giving the clinician additional information as to the effects of the modification of the value of a data point in the Paw trajectory 70.

Figure 3B:
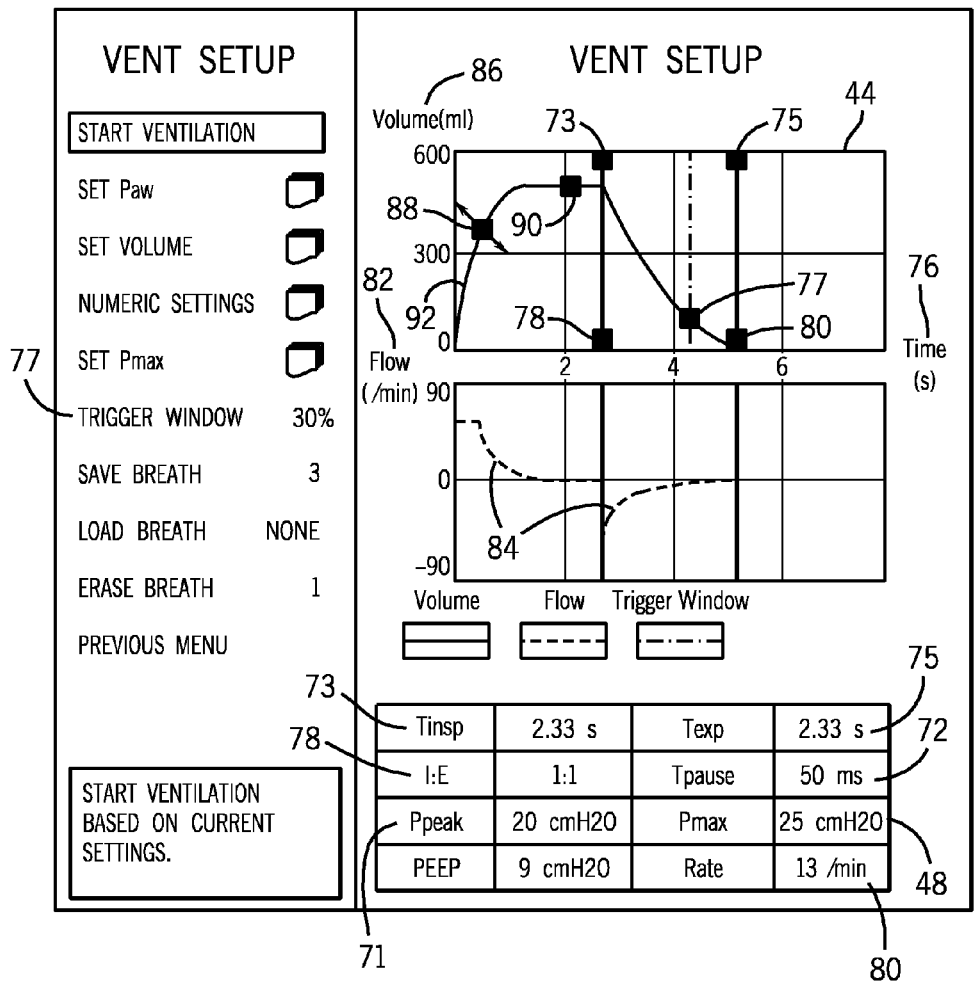
FIG. 3B depicts a screen shot of an embodiment of an interface for a clinician to create or modify a respiratory therapy volume trajectory.

Referring to FIG. 3B, an embodiment of the GUI 32 of the user interface 29 is depicted. The GUI 32 is disposed for a clinician to create a vent setup volume trajectory 92. The vent setup volume trajectory 92 is similar to the vent setup pressure trajectory 70, but instead the clinician is creating the trajectory according to a volume level 86 with respect to time 76. The volume trajectory 92 comprises a plurality of data points displayed on a graph 44. The data points may comprise actual values of the trajectory at specific times. Alternatively, as depicted in FIG. 3B, the data points are representative of particular ventilation settings that produce the volume trajectory 92. In an embodiment, the inspiration time 73, expiration time 75, I:E ratio 78, SMIV trigger window 77, and the respiration rate 80 data points are used to control the volume trajectory 92. Additionally, a curvature data point 88 and a peak volume data point 90 may be also used to control the volume trajectory 92. The curvature data point 88 is used to control the flow profile associated with the volume trajectory 92. As flow is the derivative of the volume, a diagonal line for the curvature data point 88 results in a flow that is a square wave, while a curvature data point 88 creating a square volume trajectory 92 during the inspiration time 73, would require a large initial impulse of flow. Therefore, adjustment of the curvature data point 88 gives the clinician greater control over the flow profile that results in accordance with the vent setup trajectory.

As with the pressure trajectory 70 a flow waveform 84 is created to depict the resulting flow in accordance with the vent setup volume trajectory 92 that the clinician has developed. The flow waveform 84 may be depicted in the same graph 44 as the volume trajectory 92, or may be depicted in a separate flow graph 81. The display of the flow waveform 84 gives the clinician additional feedback that changes as the clinician modifies any of the ventilation settings to modify the vent setup trajectory.

In an embodiment the data points of the vent setup display control four general categories of ventilatory settings that together define the vent setup trajectory. The four categories of ventilatory setting control are trajectory timing, trajectory amplitude, trajectory curvatures, and the trajectory trigger window. These four categories may be present in any vent setup trajectory, or a vent setup trajectory may use settings from fewer than all of the categories.

In FIGS. 3A and 3B, the inspiratory time 73, expiratory time 75, I:E ratio 78, and the respiration rate 80 are all examples of trajectory timing controls as these denote when events occur within the trajectory. The Paw data point 71 and the peak volume data point 90 are examples of the amplitude controls. The amplitude controls define the volume or pressure limits within the vent setup trajectory. Alternatively, the PEEP may be defined as an amplitude control for a vent setup trajectory. The curvature data point 88 controls the curvature of the trajectory, resulting in additional control over the flow profile delivered to the patient. The SMIV trigger window data point 77 controls when in the trajectory the ventilator begins to monitor the patient for signs of spontaneous breathing, to initiate the next inspiratory phase. Alternatively, a trajectory may include no trigger window data point 77, and accordingly a ventilator delivering respiratory therapy according to that trajectory would not monitor the patient for spontaneous breathing.

Vent setup trajectories for a single breath are depicted in FIGS. 3A and 3B; however, it is understood that within an embodiment of the present invention the vent setup trajectories may comprise one or more breaths to be delivered to a patient. In embodiments of the present invention that include multiple breaths within the vent setup trajectories, the clinician may modify pressure, flow, or time interval values for aspects of individual breaths in the trajectory to be delivered to the patient. In an embodiment of the present invention, once the clinician has established vent setup trajectory to be used in providing respiratory therapy to the patient, this trajectory specifying multiple breaths is repeated continuously to provide the respiratory therapy to the patient.

It is further understood that in an embodiment of the present invention the clinician is able to save and to name the vent setup trajectory, hereafter called templates, for the use of the same trajectory at a later date. Associated with templates are data points used to modify the trajectories of the templates such as in amplitude or time. Additionally, the newly created template may be saved at a central data location within a hospital or medical institution or the template may be saved to a portable device, such that once a trajectory has been created, named, and saved, the template may be accessible by many individuals at locations other than where the trajectory was originally created. Alternatively, a vent setup trajectory may be created on a PDA or a personal computer running the appropriate software. Alternatively, the trajectory can be constructed free form with an x-y input device. Once the vent setup trajectory is created, the trajectory may be saved such that the trajectory is accessible to be loaded into the controller of a ventilator for use in providing respiratory therapy.

In a further embodiment, the clinician may use a data knob 62 to input data into the input device 29. In an embodiment of the present invention employing a data knob 62, the clinician could modify the values of the data point by selecting one of the procedure variable buttons 27 to modify a parameter. These buttons 27 may include a set Paw button 41 which allows the Paw vertices to be set, a Numeric settings button 43 which allows the entry of values into the table 46, or a set Pmax button 45 which allows the clinician to set Pmax 48. As the clinician rotates the knob 62, a different button 27 will be highlighted. The clinician can select the highlighted button by pressing the knob 62. This will in turn highlight one of the data points. The clinician uses the same process of rotating the knob 62 to highlight the selected data point and pressing the knob 62 to select the data point. Once selected, the data point value may be changed by rotating the knob 62.

Vent Procedure Setup

The input device 29 of the present invention may also be used to operate the controller 14 to direct the ventilator 12 to operate in such a fashion as to perform a therapeutic procedure or maneuver by directing the controller to deliver medical gas to the patient according to a pressure or flow vent setup trajectory over the course of multiple breaths according to a vent procedure trajectory. For example, the patient may be suffering from atelectasis, or the collapsing of the lung. Atelactasis may be pathological as a result of COPD or ARDS, but atelactasis may also be a induced by respiratory treatment, such as delivery of 100% $O_2$, or patient sedation. Atelactasis have been associated with pulmonary shunt leading to inefficient gas exchange, alveolar wall damage through repetitive shearing of the reopening of the atelactatic tissue, and cardiac blood flow. The clinician counteracts this by applying large sustained or distending pressures to recruit the atelatatic lung and keeping the patient's lungs open at the end of each breath by applying positive end expiratory pressure (PEEP) to prevent derecruitment. However, the PEEP, as with any ventilatory pressure, must be carefully controlled because excessive pressure applied to the patient's respiratory system can cause undesirable side effects to the patient such as impeding venous return and reducing cardiac output. Other adverse side effects include excessive peak pressure that may lead to lung over distention or even rupture of alveolar sacs within the lung. Therefore, more precise techniques have been developed to control and sequence the delivery of a breath recruitment maneuver.

In an embodiment, a recruitment procedure is used in an exemplary fashion to generally describe features of the embodiment. It is understood that other types of vent procedures may be created as a vent procedure trajectory in accordance with the present invention. A recruitment procedure is directed to opening a partially collapsed lung to improve gas exchange. In a recruitment procedure, the PEEP level and peak inspiratory pressure are adjusted in a step-like fashion over the course of a series of breaths. Often, the PEEP is stepped up and then stepped down. Typically, this therapy is performed over the course of about two to ten minutes of patient ventilation, but may extend longer. In some lung recruitment procedures, Ptot is also increased in relation to the change in the PEEP level. The application of a lung recruitment procedure has the effect of filling the patient's lungs to a greater extent with each progressive step in pressure, thereby exposing more alveoli to medical gas and prompting improved gas exchange. Examples of other procedures that will not be described in detail are suctioning, weaning, and spontaneous breathing trial.

Figure 4A:
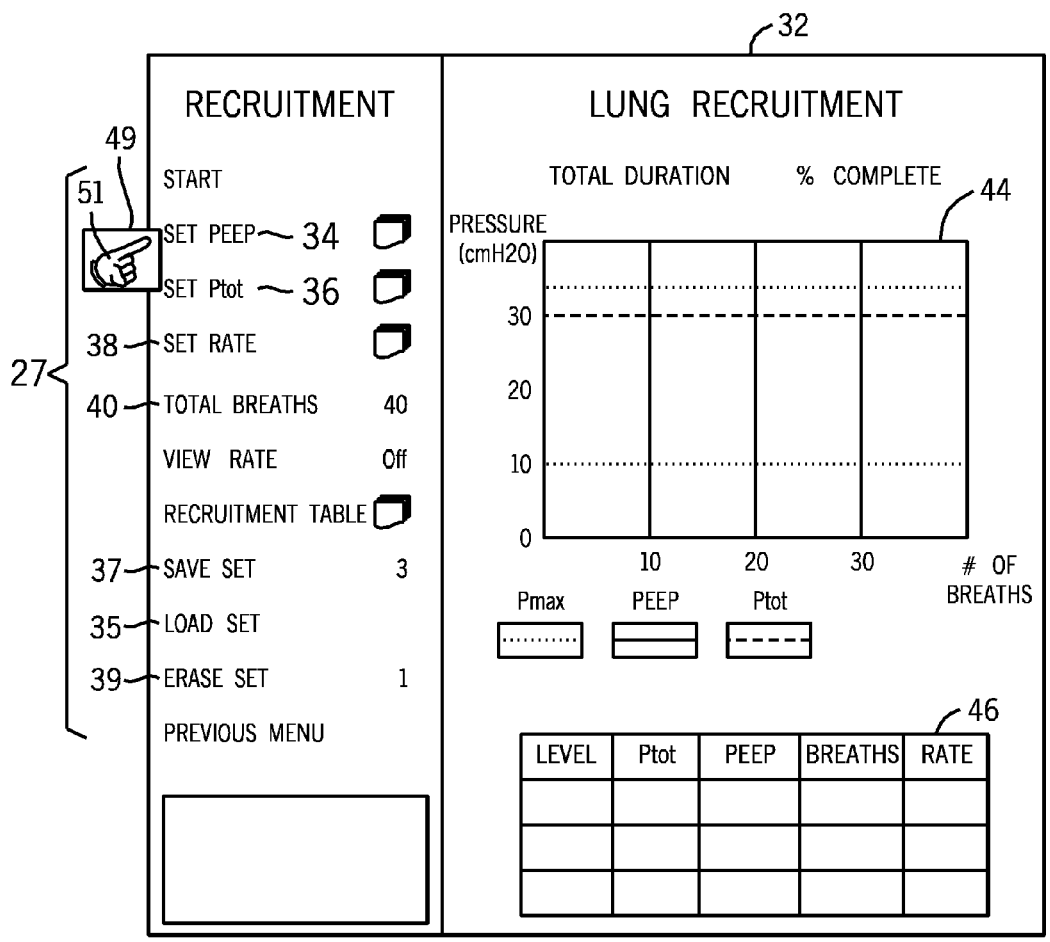
FIGS. 4A-E depict a series of screen shots in reference to an interface of the present invention for a clinician to create or modify a ventilation therapy procedure.
Figure 4B:
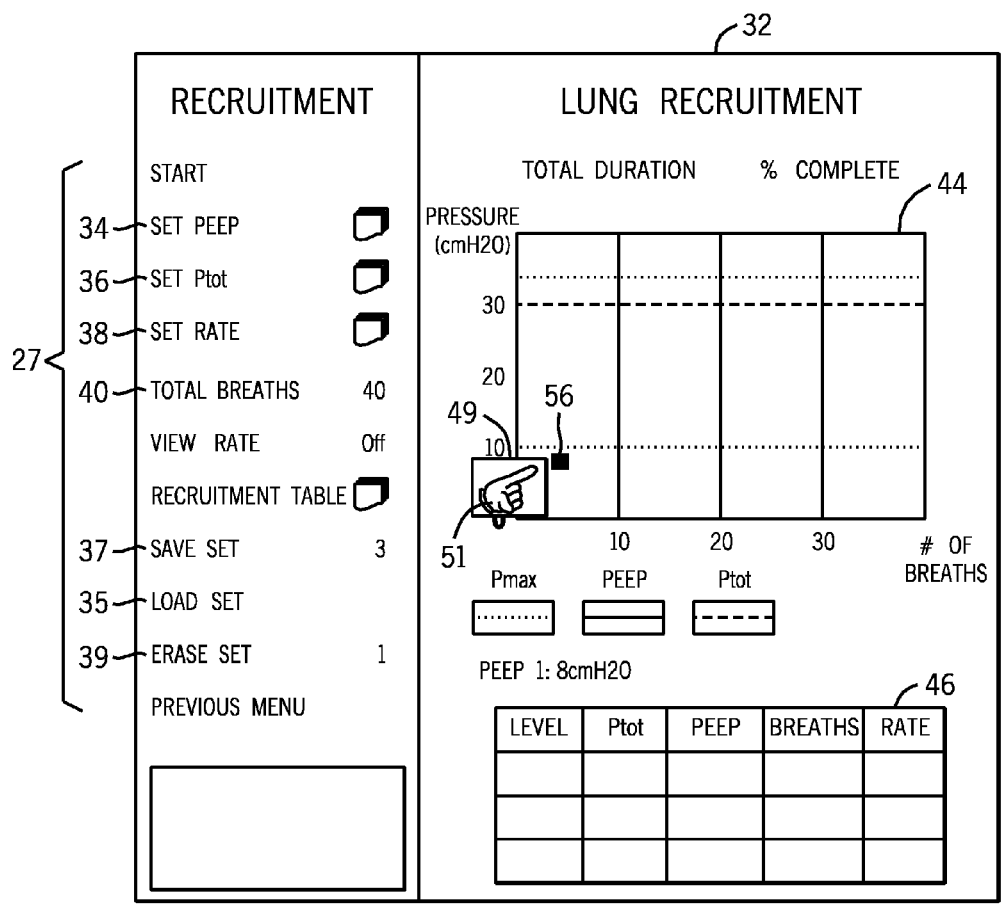
Figure 4C:
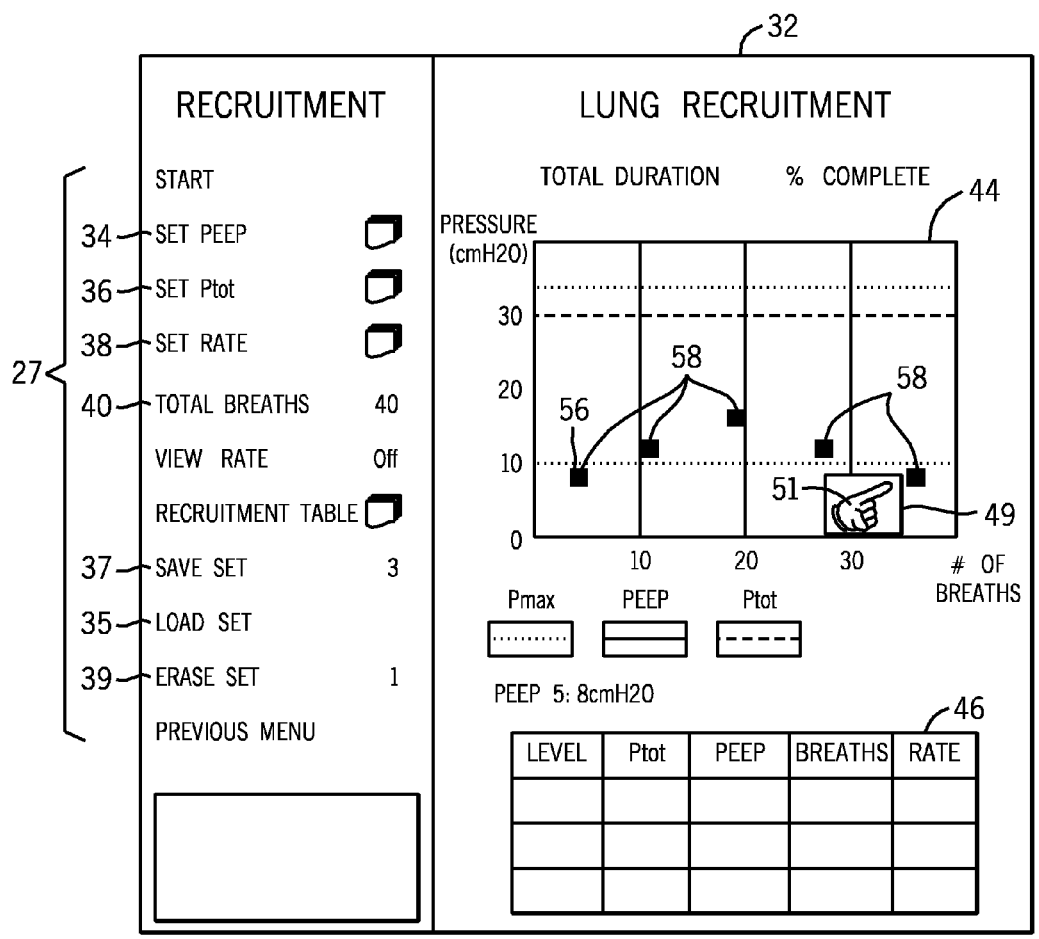
Figure 4D:
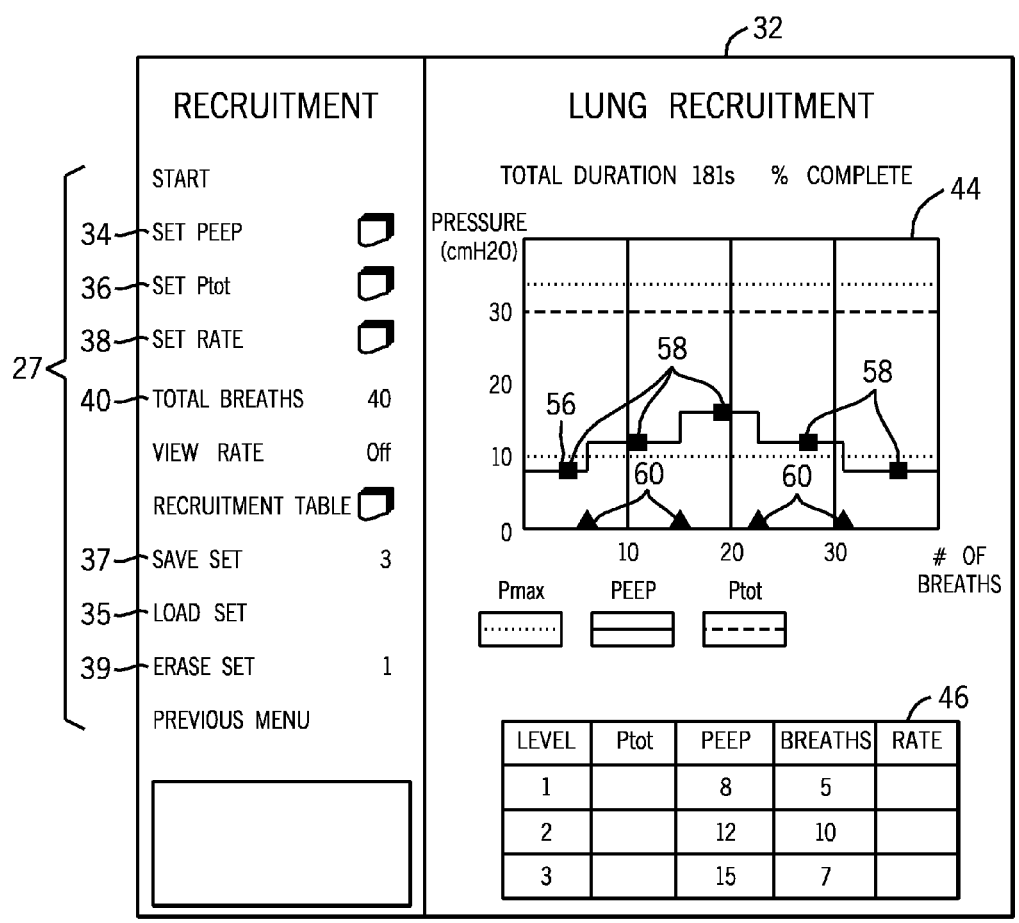

Referring now to FIGS. 4A-E, FIG. 4 depicts through a series of screen shots of the GUI 32 an embodiment of the present invention by describing an interaction between the clinician and the input device 29 to create a recruitment procedure that consist of a sequence of vent setup trajectories. In this embodiment, the clinician uses an input means associated with the input device 29, such as a mouse or a touch screen, to enter the desired procedure trajectory data. As depicted in FIG. 4A, the clinician will select, with a cursor 49 or physically with his finger 51 or a stylus (not depicted), the procedure variable buttons 27 that the clinician wants to set for the recruitment procedure trajectory, in this case the set PEEP button 34. The clinician may also set the Ptot value 36, the breathing rate 38, and the total number of breaths 40 for the entire procedure. Next, depicted in FIG. 4B, the clinician interacts with the graph 44 to place a data point 56 to set the approximate location for the first PEEP step. The value for the first PEEP step is set this way because the clinician has selected the set PEEP button 34. FIG. 4C depicts the GUI display after the clinician has continued this process of setting data points 58 to establish the PEEP level for each of the PEEP steps desired for the procedure. Upon completion of setting the approximate location for all of the PEEP steps, a vent procedure trajectory 50 is generated that encompasses each of the PEEP steps established by the clinician, as depicted in FIG. 4D. The lung recruitment variable values for the generated vent procedure trajectory 50 are inserted into the table 46.

Figure 4E:
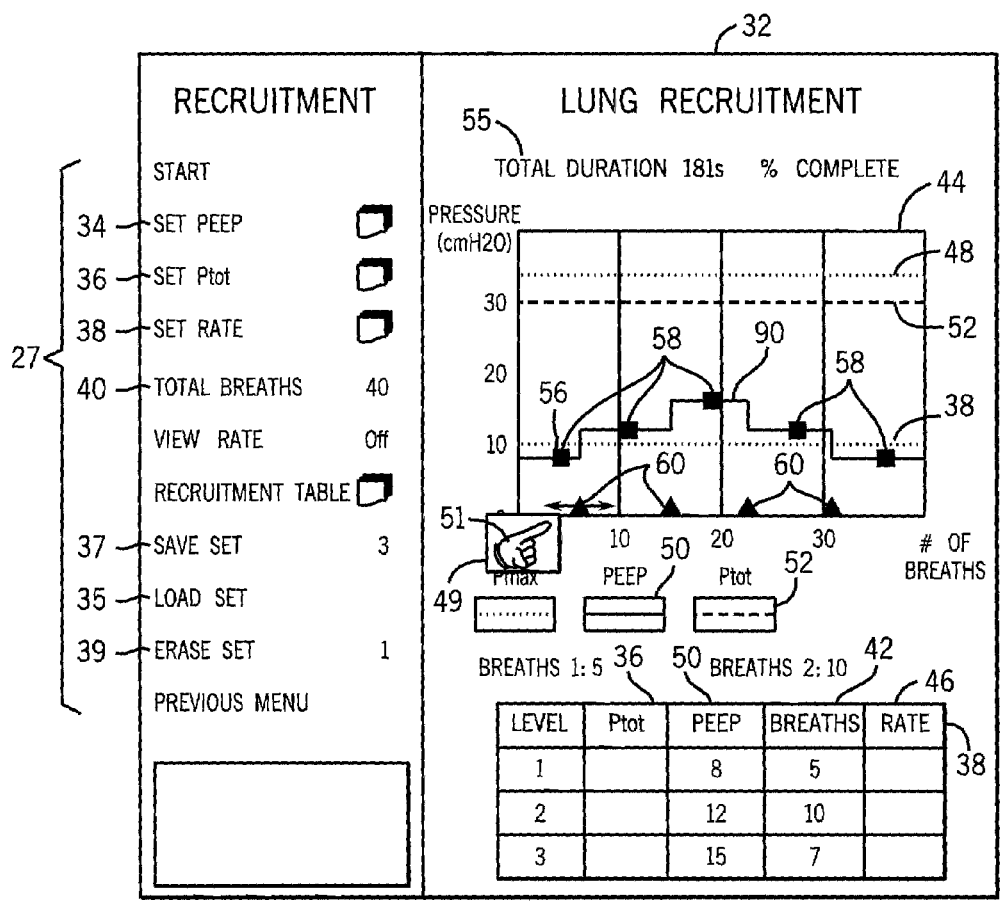

The vent procedure trajectory 50 depicted in FIG. 4E comprises data points for the modification of two trajectory variables: PEEP value 58 and number of breaths 60. Upon viewing the values of the automatically created procedure trajectory 50, the clinician can then modify the values of the data points. The clinician can select a PEEP data point and increase or decrease the PEEP pressure for each step of the procedure trajectory 50. The clinician can increase or decrease the number of breaths for each PEEP step in the procedure trajectory 50 by selecting the breath number data point 60 associated with that step. As the clinician changes these values, the graph 44 changes to show the currently modified trajectory. Additionally, a display of total procedure duration 55 is computed to inform the clinician of the length of the procedure that he has currently created. In this respect, the clinician is able to view the specific effects that a change to the variable corresponding to one data point has on the values of other related variables. Also, the graphic display gives the clinician greater control over the value of the lung recruitment variables such that the clinician can specifically tailor a therapy to an individual patient based upon their specific physiological characteristics, for example, lung capacity or lung compliance. In general, a variety of respiratory therapy trajectories such as described above may be obtained from a library of previously stored template.

In an embodiment of the present invention, the x-axis of the graph 44 comprises both time and number of breath indices. In an embodiment, the spacing of the time indices remains constant while the breath indices conform or distort to accurately reflect the respiration rate at a particular PEEP step. For an example of this embodiment, areas of a high respiration rate will have breath indices marked close together as more breaths are occurring with respect to time, while areas of a low respiration rate will have breath indices further apart. Such representative illustration emphasize and simplifies the display of the vent procedure trajectory, while the detailed vent procedure trajectories are illustrated or can be constructed through the template, as needed.

The graphical representation of the ventilation parameters in graph 44 provides the clinician with a tool to intuitively enter ventilator parameter values and observe the effects of the values chosen. Also, values from the table 46 that correspond to the visual display in the graph 40 help to convey the information to the clinician. This data includes the total pressure (Ptot) 36, the respiration rate 38, the number of breaths 42, the maximum pressure (Pmax) 48, and the PEEP pressure 50. As previously stated, adverse effects can occur to the patient if excessive pressures are delivered to the patient's lungs. Therefore, as an example of the intuitiveness of the display, while the clinician may know the boundary of maximum pressure to be delivered to the patient is (Pmax) 48, the clinician may forget or may accidentally enter wrong value of Ptot 36. The clinician will become aware of this mistake when the clinician views the graph 44 after the graph 44 updates to include the new Ptot value in the Ptot graph 52. If the Ptot graph 52 ever exceeds the Pmax graph 48, the clinician knows that a new Ptot value 36 must be entered, one that does not exceed Pmax 48. Alternatively, in an embodiment of the present invention, the user interface 29 or vent controller 14 does not allow the clinician to enter a value that exceeds a predetermined threshold limit. The user interface 29 would stop receiving changes to a parameter by a clinician that exceed a threshold value; this would also be indicated on the display as the graphical depiction of the value would also not increase.

The calculation of the total duration 55 of the procedure may be displayed to the clinician. As the clinician enters values for the total number of breaths 42 and the respiration rate 38, he may not be performing the calculations to know how long the procedure will last. These calculations become complex when the respiration rate 38 changes for different increments of PEEP pressure. Therefore, the clinician may not be aware of the duration of the procedure that the patient is about to under go. The total duration 55 calculation updates as the clinician changes procedure variables, providing the clinician with up-to-date information regarding the total time of the recruitment procedure he is about to initiate.

Once the clinician has created a desirable vent procedure trajectory, the clinician may save the vent procedure trajectory for use at a later date by selecting the save button 37. The clinician may then name the vent procedure trajectory and save it to that specific input device 29, to a centralized data storage unit (not depicted) as part of an IT network of a clinical facility, or to a portable data storage device such as a PDA or a memory stick. This saved vent procedure trajectory may then be recalled and initiated on a ventilator by the clinician or another clinician. Alternatively, the vent procedure trajectory may be created on a personal computer or a PDA running the appropriate software. Once a vent procedure trajectory is created, it may be saved such that the trajectory is accessible to be loaded into the input device 29 of a ventilator 12 for use in providing respiratory therapy.

Figure 5:
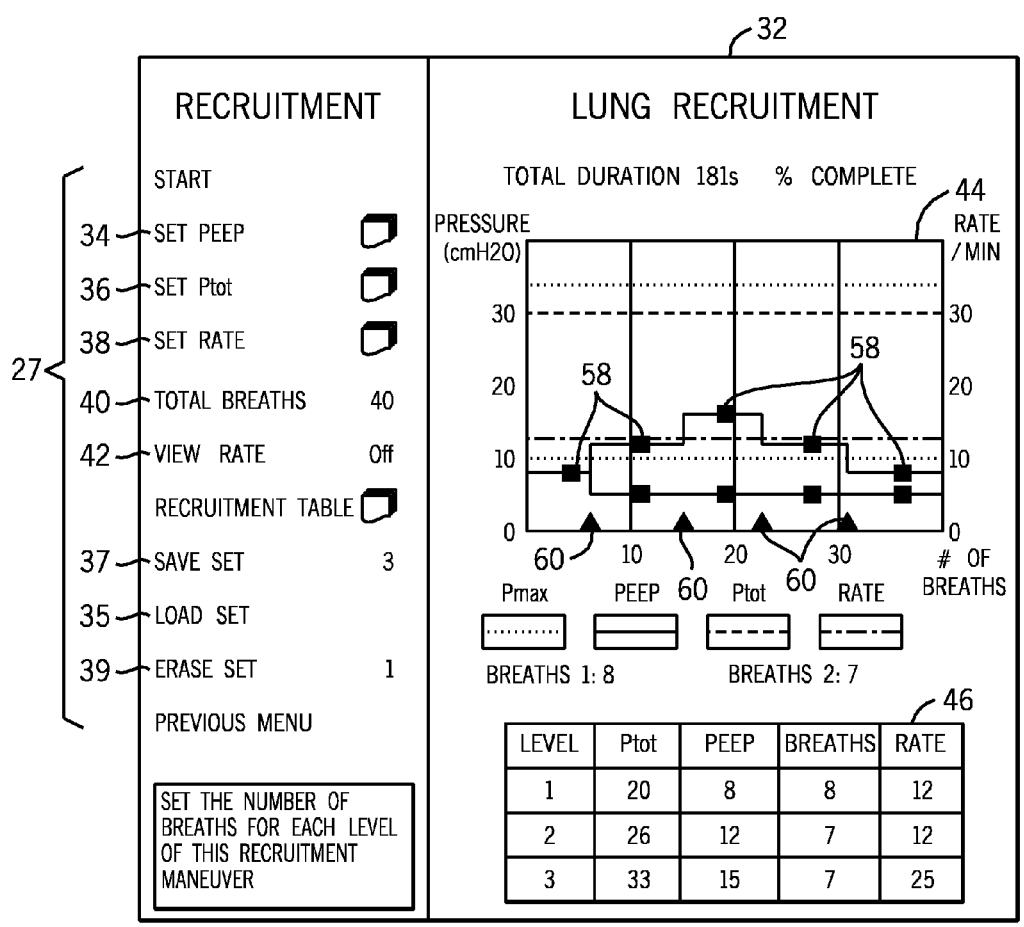
FIG. 5 depicts a screen shot of an embodiment of the GUI of the present invention.

An alternative embodiment of the present invention is depicted in reference to FIGS. 2 and 5. FIG. 5 depicts a screen shot of a GUI 32 of the present invention. In this embodiment of the present invention, the clinician may select a saved or model vent procedure trajectory by selecting the load trajectory button 35. The vent procedure trajectory and associated procedure variable values will be displayed in both the graph 44 and the table 46 as depicted in FIG. 5. The clinician can then use the data knob 62 of the input device 29 as depicted in FIG. 2 to select one of the procedure variable buttons 27 to modify either the PEEP data points 58 or the breath data points 60. After the selection has been made, the clinician can rotate the data knob 62 to further select the specific data point to modify. The clinician may then modify the value of that lung recruitment variable by rotating the knob 62 again.

Figure 6:
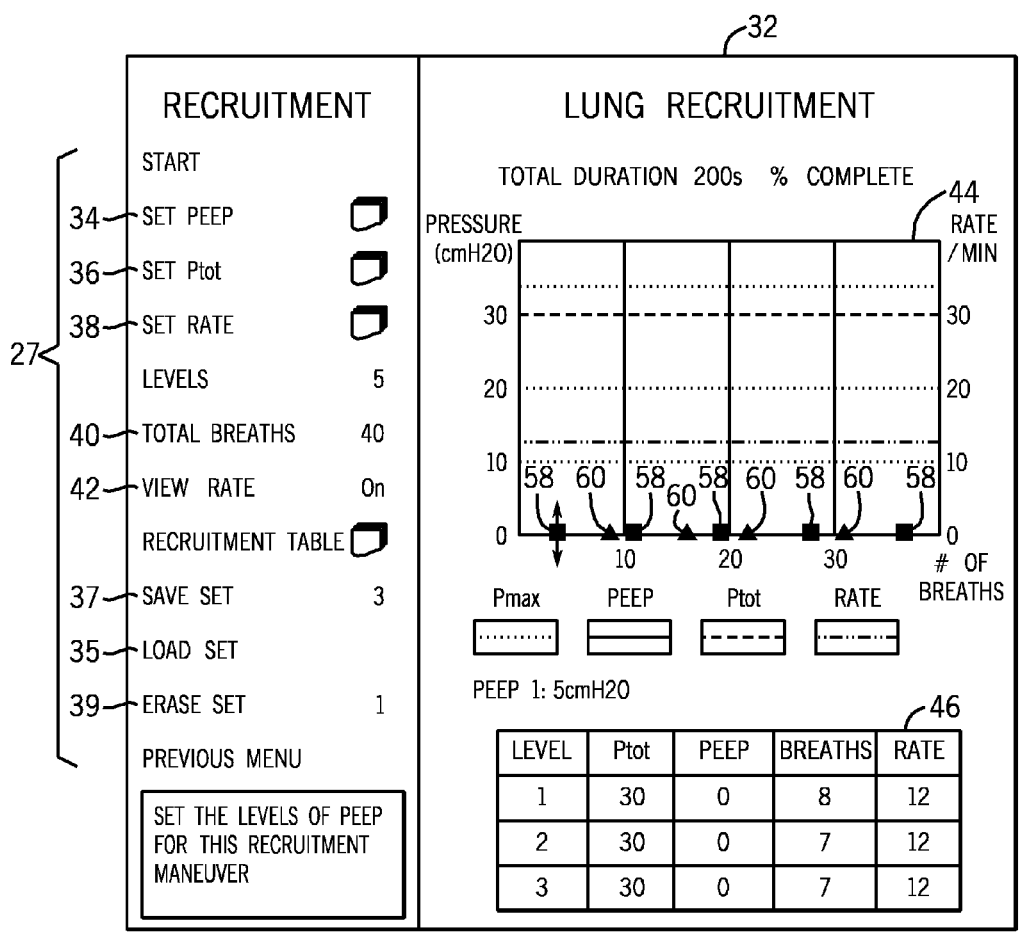
FIG. 6 depicts a screen shot of an embodiment of the GUI of an embodiment of the present invention.

In an alternative embodiment of the present invention, depicted in FIG. 6, the clinician may select the set levels control 40 to establish the number of PEEP therapy levels for the vent procedure trajectory. The GUI 32 of this embodiment of the present invention will then create a blank vent recruitment procedure with PEEP data points 58 and breath number data points 60 for each of the levels identified. The clinician can then select each of the PEEP 58 and breath number 60 data points in turn to create a new vent recruitment trajectory. This trajectory may then be saved by selecting the save button 37 to be recalled at a later time to provide this vent procedure trajectory again.

Method

Figure 7:
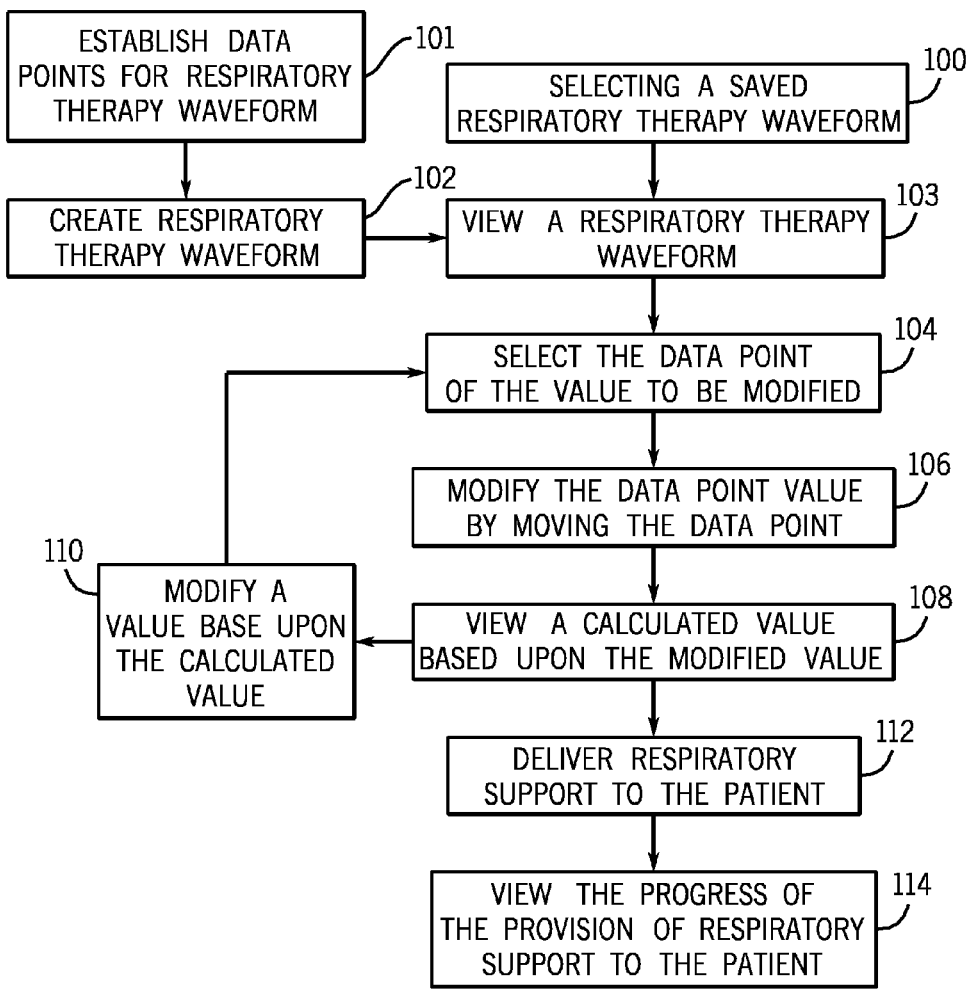
FIG. 7 depicts a flow chart of the method in accordance with an embodiment of the present invention.

FIG. 7 is a flow chart that depicts the steps of an embodiment of the method of the present invention. The clinician begins by selecting a saved respiratory therapy trajectory, or template, in step 100, to use for controlling the delivery of respiratory therapy to the patient. The template may be a trajectory for a selected vent setup, such as volume controlled ventilation, or a vent procedure, such as a recruitment procedure. The template may also be created by the clinician or it may be institutionally created and saved to a centrally available institutional data storage, such as the server of a hospital. Alternatively, the clinician may create a respiratory therapy trajectory by establishing data points in step 101. The clinician may establish these data points by any number of data input methods such as drag and drop, arrow keys, dialing a knob on the controller, or using a touch screen; however, many other suitable data input methods may be used within the present invention. Once the data points have been established by the clinician, the respiratory therapy trajectory, is created in step 102. Optionally, this new respiratory therapy trajectory, may be saved to be accessed at a later time as a template in step 100.

After the template has been selected in step 100, or created in step 102, the clinician views the respiratory therapy trajectory in step 102. The trajectory may also include a display of all the relevant variables required to the control of the desired respiratory therapy. In the example of a lung recruitment procedure, the trajectory display may include the display of the variables of Pmax, PEEP, breath rate, and total number of breaths. The clinician views the trajectory looking for data point values that the clinician desires to modify and specifically tailor the respiratory therapy trajectory to the patient.

Next, the clinician selects the data point that is associated with the value that is to be modified in step 104. In step 106, the clinician modifies that data point value by moving the data point. The clinician may move the data point in a variety of ways that a clinician may interact with a graphic that is displayed on a display. As the clinician modifies the value by moving the data point in step 106, new values are calculated that are dependent upon the value that the clinician is modifying. The calculated value is then viewed in step 108 so that the clinician can view the new value that has been affected by the modification of the data point value in step 106. Therefore, in step 110, the clinician is able to modify that same value or another value based upon the calculated values viewed in step 108. The clinician repeats steps 104 through 110 until the clinician views the respiratory therapy trajectory in step 108 and determines that the proper respiratory therapy trajectory to deliver to the patient has been achieved.

Upon creating a respiratory therapy trajectory that is specifically tailored to the patient in steps 100-110, the clinician initiates the delivery of the respiratory therapy to the patient in step 112. The controller 14 of the ventilator 12 controls the delivery of the therapy to the patient according to the trajectory. Finally, while the respiratory therapy is being delivered, the clinician can view the progression of the respiration therapy on a display. By viewing a graphical representation of the trajectory as well as the measured waveform of the actual respiratory therapy being delivered to the patient, the clinician can monitor the changes in specific patient physiological parameters in relation to the progression of the respiratory therapy. The respiratory therapy progression may be displayed as a graphical representation comprising a timebar or a color change to denote progress. Alternatively, the trajectory can be displayed in its entirety with the waveform updating in real-time aligned with the trajectory.

In embodiments of the present invention, other patient parameters may be displayed along with the respiratory therapy trajectory progression display. For example, a graph of a measured patient physiological parameter such as lung volume could be displayed along with the progression of the recruitment procedure. The display of the representative progress displayed in combination with patient lung volume offers a quick assessment of the effectiveness or inappropriateness of the recruitment procedure to continue, abort, or otherwise modify the vent procedure. In general, the embodiments of the present invention allow for the intelligent development or establishment of new respiratory therapy trajectories by a clinician, a group of clinicians, or a whole healthcare institution.

The present invention holds advantages over the field of mechanical ventilation controllers because it provides an intuitive, graphically based interface where clinicians can modify the value of a parameter of a respiratory therapy trajectory and be presented with the effects of the selection of that new value. This improves the clinician's overall awareness of the effects of a respiratory therapy trajectory enabling the clinician to improve the respiratory treatment over time and to individually tailor the respiratory treatment to the patient in accordance to the respiratory therapy trajectory.

The present invention provides the advantage of improved feedback and control of respiratory therapy trajectories to control the medical gas waveforms provided to a patient. The trajectories may be saved and accessible by many clinicians and evaluated based upon the effectiveness of the respiratory therapy provided. Therefore, the quality of the trajectories may be improved as the trajectories are used over time and clinicians evaluate the effectiveness and modify the trajectories. Furthermore, the present invention allows a clinician or an institution to develop preferred trajectories that may be used repeatedly. Another advantage is that the increased clinician and institutional control of the trajectories provided by the embodiments of the present invention allow a clinician to update the trajectories to reflect current medical research without expensive software updates to the ventilator controller. In this respect, a clinician or institution merely needs to create a new trajectory based on knowledge of improved treatments.

Furthermore, the present invention provides the clinician with greater ease of use of the mechanical ventilator, promoting clinician efficiency in the implementation of respiratory therapy trajectories. The present invention provides an easy way to enter a desired respiratory therapy trajectory and control the necessary ventilation variables to modify the treatment to fit the individual patient. Additionally, an embodiment of the present invention has the further advantage of working over the controller 14 for the ventilator 12 such that the operation and commands used by the input device 29 of the present invention work the same irrespectively of the underlying ventilator 12 that is being controlled. This embodiment improves a clinician's ability to operate many types of ventilators that may or may not use the same nomenclature, controls and/or parameters to establish similar respiratory therapy techniques.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

We claim:
1. A method of controlling a mechanical ventilator to deliver respiratory therapy to a patient, the method comprising the steps of:
  presenting a vent procedure trajectory comprising a plurality of data points representative of ventilator control values presented in an at least two-dimensional coordinate system on a graphical display wherein each data point is representative of at least one respiratory cycle in the vent procedure trajectory;
  receiving a selection of a data point from the plurality of data points;

receiving, a modification to a location of the selected data point in the two-dimensional coordinate system to modify a ventilator control value associated with the selected data point;

recalculating the ventilator control value associated with the selected data point based upon the modified value of the selected data point;

presenting a modified vent procedure trajectory in response to the recalculated ventilator control value associated with the selected data point; and controlling a mechanical ventilator to deliver medical as to the patient across a plurality of respiratory cycles according to the ventilator control values represented by the modified vent procedure trajectory.

2. The method of claim 1 further comprising the step of selecting a saved vent procedure trajectory.

3. The method of claim 2 wherein the saved vent procedure trajectory is saved on a centralized data storage accessible via a network.

4. The method of claim 1 further comprising the steps of:
initiating the delivery of the medical gas for a plurality of respiratory cycles to the patient according, to the vent procedure trajectory; and presenting a graphical indication of the progress of the delivery of the medical gas according to the vent procedure trajectory on the graphical display.

5. The method of claim 4 wherein the graphical indication of the progress of the delivery of the medical gas according to the vent procedure trajectory comprises a display of a completed portion of the vent procedure trajectory and a display of at least one patient physiological parameter.

6. The method of claim 5 wherein the display of the completed portion of the vent procedure trajectory and at least one patient physiological parameter comprises displaying a waveform resulting from the delivery of medical gas to the patient according to the vent procedure trajectory.

7. The method of claim 1 wherein the vent procedure trajectory is a recruitment procedure trajectory.

8. A user interface for controlling a mechanical ventilator, the mechanical ventilator configured to deliver medical gas to a patient, the user interface comprising:
a graphical display;
a vent setup trajectory presented on the graphical display, the vent setup trajectory defines the delivery of medical gas to the patient over a respiratory cycle with a first plurality of graphical data points in at least it two-dimensional coordinate system representative of a first venti-lator operational parameter and a second ventilator operational parameter;
a vent, procedure trajectory presented on the graphical display, the vent procedure trajectory defines the delivery of medical as to the patient over a plurality of respiratory cycles defined by the vent setup trajectory with a second plurality of graphical data points in at least a two-dimensional coordinate system representative of a first vent procedure variable and a second vent procedure variable, each graphical data point of the second plurality of graphical data points representative of at least one respiratory cycle in the vent procedure trajectory;
an input device that receives a first user input modifying a value of one of the first plurality of graphical data points and receives a second user input modifying a value of one of the second plurality of graphical data points; and
a controller operationally connected to the mechanical ventilator, wherein the controller operates the mechanical ventilator to deliver medical gas to the patient according to the vent setup trajectory and the vent procedure trajectory.

9. The user interface of claim 8 wherein the first ventilator operational parameter is selected from medical gas pressure, medical gas volume, and medical gas flow.

10. The user interface of claim 9 wherein the second ventilator operational parameter is a time of a single respiratory cycle.

11. The user interface of claim 8 wherein the first vent procedure variable is PEEP and the second vent procedure variable is a number of respiratory cycles.

12. The user interface of claim 8 wherein each of the graphical data points of the first and second plurality of graphical data points are related by at least one algorithm such that numerical values of the first and second plurality graphical data points are modified in response to the modification of a value of one of the first and second plurality graphical data points.

13. The user interface of claim 8 wherein the first ventilator operational parameter is a medical gas pressure and the second ventilator operational parameter is time.

14. In a computer system having a graphical user interface including a display and a selection device, a method of controlling, a mechanical ventilator to provide medical gas to a patient, the method comprising:
presenting a plurality of data points representing a vent procedure trajectory in at least a two-dimensional coordinate system, each of the plurality of data points representing a vent setup trajectory and a ventilator parameter value in the vent procedure trajectory;
receiving a user input entry signal selecting a selected data point of the plurality of data points;
in response to the user input entry signal, moving the selected data point in the at least two-dimensional coordinate system; and
in response to the user input entry signal, adjusting the ventilator parameter value presented by the selected data point.

15. The method of claim 14 comprising operating the mechanical ventilator to provide medical gas to the patient according to the ventilator parameters represented by the data points of the vent procedure trajectory.

16. The method of claim 14 further comprising:
receiving user input entry signals indicating a selected plurality of vent setup trajectories, each vent setup trajectory of the selected plurality represented by a data point of the vent procedure trajectory, wherein the selected plurality of vent setup trajectories are stored in a storage device.

17. The method of claim 14 further comprising:
receiving user input entry signals indicating a selected plurality of vent setup trajectories each vent setup trajectory of the selected plurality represented by a data point of the vent procedure trajectory, wherein the selected plurality of vent setup trajectories sequentially operate the mechanical ventilator to increase the positive end expiration pressure (PEEP) of the patient in a lung volume recruitment procedure.

18. The method of claim 14 wherein the vent setup trajectory is one of a plurality of vent setup trajectories, and further comprising:
presenting a plurality of data points representing a selected vent setup trajectory of the plurality of vent setup trajectories, each of the data points of the plurality of data points representing the selected vent setup trajectory represent a ventilator parameter value in the selected vent setup trajectory;

receiving a user input entry signal selecting a selected data point of the plurality of data points representing the selected vent setup trajectory;

modifying a ventilator parameter value represented by the selected data point; and saving the modified ventilator parameter value in a modified vent setup trajectory in the plurality of vent setup trajectories;

wherein the modified vent setup trajectory is represented by at least one of the plurality of data points in the vent procedure trajectory.

* * * * *